US009486611B2

(12) United States Patent
Petersen et al.

(10) Patent No.: US 9,486,611 B2
(45) Date of Patent: Nov. 8, 2016

(54) GUIDE EXTENSION CATHETER

(71) Applicant: BOSTON SCIENTIFIC SCIMED, INC., Maple Grove, MN (US)

(72) Inventors: Eric M. Petersen, Maple Grove, MN (US); Steven R. Larsen, Lino Lakes, MN (US); Wayne Falk, Minneapolis, MN (US); Joel M. Wasdyke, Eden Prairie, MN (US); Huisun Wang, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 108 days.

(21) Appl. No.: 13/969,390

(22) Filed: Aug. 16, 2013

(65) Prior Publication Data
US 2014/0052097 A1 Feb. 20, 2014

Related U.S. Application Data

(60) Provisional application No. 61/684,591, filed on Aug. 17, 2012.

(51) Int. Cl.
*A61M 25/01* (2006.01)
*A61M 25/09* (2006.01)
A61M 25/00 (2006.01)

(52) U.S. Cl.
CPC ......... *A61M 25/01* (2013.01); *A61M 25/0023* (2013.01); *A61M 25/0069* (2013.01); *A61M 25/0074* (2013.01); *A61M 25/09* (2013.01); *A61M 25/007* (2013.01);
(Continued)

(58) Field of Classification Search
CPC ................... A61M 25/0172; A61M 25/0023; A61M 25/0074; A61M 2025/0175; A61M 2025/018; A61M 2025/0025; A61M 2025/0183; A61M 25/0662; A61M 25/0067; A61M 25/01; A61M 25/09; A61M 25/0069; A61M 25/0052; A61M 25/0013; A61M 25/007; A61M 25/0045; A61M 2025/0004
USPC .............. 604/103.04, 164.03, 523, 528, 151, 604/164.08, 180, 198; 600/585
See application file for complete search history.

(56) References Cited

U.S. PATENT DOCUMENTS 4,564,014 A 1/1986 Fogarty et al.
4,616,652 A 10/1986 Simpson
(Continued)

FOREIGN PATENT DOCUMENTS

DE 3819372 C1 1/1990
EP 0277366 A1 8/1988
(Continued)

*Primary Examiner* — Andrew Gilbert
*Assistant Examiner* — Amber Stiles
(74) *Attorney, Agent, or Firm* — Seager, Tufte & Wickhem, LLP

(57) ABSTRACT

Medical devices and methods for making and using medical devices are disclosed. An example medical device may include a guide extension catheter. The guide extension catheter may include an elongate tubular member having a proximal region, a distal region, and a slot formed in the tubular member between the proximal region and the distal region. The proximal region of the tubular member may be configured to shift between a first configuration and a collapsed configuration. The guide extension catheter may also include an elongate shaft for shifting the proximal region between the first configuration and the collapsed configuration.

11 Claims, 19 Drawing Sheets

(52) U.S. Cl.
CPC ..... *A61M 25/0013* (2013.01); *A61M 25/0045* (2013.01); *A61M 25/0052* (2013.01); *A61M 2025/0004* (2013.01); *A61M 2025/0025* (2013.01)

(56) References Cited

U.S. PATENT DOCUMENTS

| | | | |
|---|---|---|---|
| 4,762,129 A | 8/1988 | Bonzel | |
| 5,102,402 A * | 4/1992 | Dror | A61F 2/958 604/103.02 |
| 5,106,455 A | 4/1992 | Jacobsen | |
| 5,120,323 A | 6/1992 | Shockey et al. | |
| 5,232,445 A | 8/1993 | Bonzel | |
| 5,238,004 A | 8/1993 | Sahatjian et al. | |
| 5,267,982 A | 12/1993 | Sylvanowicz | |
| 5,385,562 A | 1/1995 | Adams et al. | |
| 5,441,489 A | 8/1995 | Utsumi et al. | |
| 5,527,292 A | 6/1996 | Adams et al. | |
| 5,772,609 A | 6/1998 | Nguyen | |
| 6,007,522 A * | 12/1999 | Agro et al. | 604/264 |
| 6,066,126 A | 5/2000 | Li et al. | |
| 6,139,510 A | 10/2000 | Palermo | |
| 6,508,803 B1 | 1/2003 | Horikawa et al. | |
| 6,575,958 B1 | 6/2003 | Happ et al. | |
| 6,579,246 B2 | 6/2003 | Jacobsen | |
| 6,638,268 B2 | 10/2003 | Niazi | |
| 6,695,793 B2 | 2/2004 | Brennan et al. | |
| 6,766,720 B1 | 7/2004 | Jacobsen | |
| 6,953,454 B2 | 10/2005 | Peterson et al. | |
| 7,294,124 B2 | 11/2007 | Eidenschink | |
| 7,309,334 B2 * | 12/2007 | von Hoffmann | A61B 17/22 604/524 |
| 7,316,678 B2 | 1/2008 | Nash et al. | |
| 7,717,899 B2 | 5/2010 | Bowe et al. | |
| 7,762,984 B2 | 7/2010 | Kumoyama et al. | |
| 8,048,032 B2 | 11/2011 | Root et al. | |
| 8,142,413 B2 | 3/2012 | Root et al. | |
| 8,292,850 B2 | 10/2012 | Root et al. | |
| 8,298,178 B2 | 10/2012 | Carrillo et al. | |
| 2003/0023229 A1* | 1/2003 | Kramer | 604/523 |
| 2003/0050600 A1* | 3/2003 | Ressemann | A61B 17/12109 604/101.01 |
| 2003/0069522 A1 | 4/2003 | Jacobsen et al. | |
| 2003/0100849 A1* | 5/2003 | Jang | A61M 25/0023 600/585 |
| 2004/0116832 A1 | 6/2004 | Friedrich et al. | |
| 2004/0181174 A2 | 9/2004 | Davis | |
| 2006/0079859 A1* | 4/2006 | Elkins | A61M 25/00 604/508 |
| 2006/0235458 A1* | 10/2006 | Belson | A61M 25/0032 606/191 |
| 2007/0260219 A1* | 11/2007 | Root et al. | 604/523 |
| 2008/0181174 A1 | 7/2008 | Cho | |
| 2009/0099550 A1* | 4/2009 | Carrillo | A61B 1/018 604/528 |
| 2009/0999550 | 4/2009 | Carrillo et al. | |
| 2009/0177120 A1 | 7/2009 | Tockman et al. | |
| 2011/0004197 A1* | 1/2011 | Sansoucy | 604/523 |
| 2011/0112564 A1* | 5/2011 | Wolf | A61M 25/0069 606/159 |
| 2011/0160834 A1* | 6/2011 | Aggerholm | A61F 2/958 623/1.11 |
| 2011/0301502 A1 | 12/2011 | Gill et al. | |
| 2013/0053766 A1* | 2/2013 | Hollett | A61M 25/0069 604/95.01 |

FOREIGN PATENT DOCUMENTS

| | | |
|---|---|---|
| EP | 0564894 A1 | 10/1993 |
| WO | 03049798 A2 | 6/2003 |
| WO | 2005018728 A2 | 3/2005 |

* cited by examiner

GUIDE EXTENSION CATHETER

CROSS-REFERENCE TO RELATED APPLICATIONS

This application claims priority under 35 U.S.C. §119 to U.S. Provisional Application Ser. No. 61/684,591, filed Aug. 17, 2012, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a guide extension catheter.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a guide extension catheter. The guide extension catheter may include an elongate tubular member having a proximal region, a distal region, and a slot formed in the tubular member between the proximal region and the distal region. The proximal region of the tubular member may be configured to shift between a first configuration and a collapsed configuration. The guide extension catheter may also include an elongate shaft for shifting the proximal region between the first configuration and the collapsed configuration A method for using a guide extension catheter is also disclosed. The method may include providing a guide catheter, advancing the guide catheter through a body lumen to a position adjacent to an area of interest, and advancing a guide extension catheter through the guide catheter. The guide extension catheter may include an elongate tubular member having a proximal region, a distal region, and a slot formed in the tubular member between the proximal region and the distal region. The proximal region of the tubular member may be configured to shift between a first configuration and a collapsed configuration. The guide extension catheter may also include an elongate shaft for shifting the proximal region between the first configuration and the collapsed configuration. The method may include shifting the proximal region from the first configuration to the collapsed configuration and advancing a treatment through the distal region of the tubular member to a position adjacent to the area of interest.

A guide extension catheter system is also disclosed. The system may include a guide catheter and a guide extension catheter configured to extend through the guide catheter. The guide extension catheter may include an elongate tubular member having a proximal region, a distal region, and a slot formed in the tubular member between the proximal region and the distal region. The proximal region of the tubular member may be configured to shift between a first configuration and a collapsed configuration. The guide extension catheter may also include an elongate shaft for shifting the proximal region between the first configuration and the collapsed configuration. The system may also include a treatment catheter configured to extend through the guide catheter and through the distal region of the tubular member.

Another example guide extension catheter may include a tubular body having a proximal portion and a distal portion. The proximal portion may include a partially circumferential arcuate wall. The distal portion may include a fully circumferential arcuate wall.

Another example guide extension catheter may include a proximal shaft having a proximal outer diameter. A distal sheath may be attached to the proximal shaft. The distal sheath may have a distal outer diameter greater than the proximal outer diameter. A collar may be attached to the proximal shaft and to the distal sheath. The collar may have a plurality of slots formed therein.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
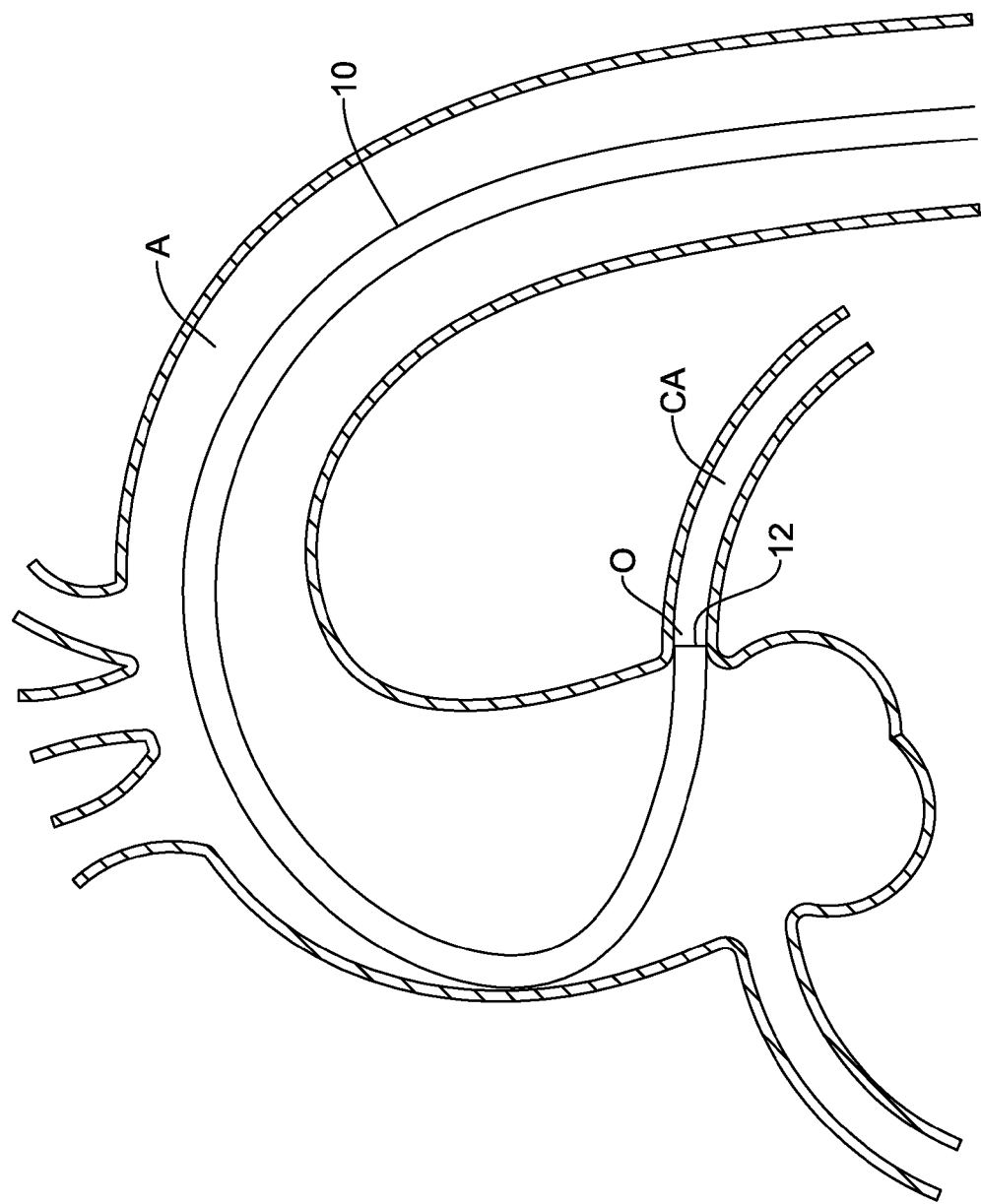
FIG. 1 is a plan view illustrating an example guide catheter advanced through the aorta to the ostium of a coronary artery.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Figure 2:
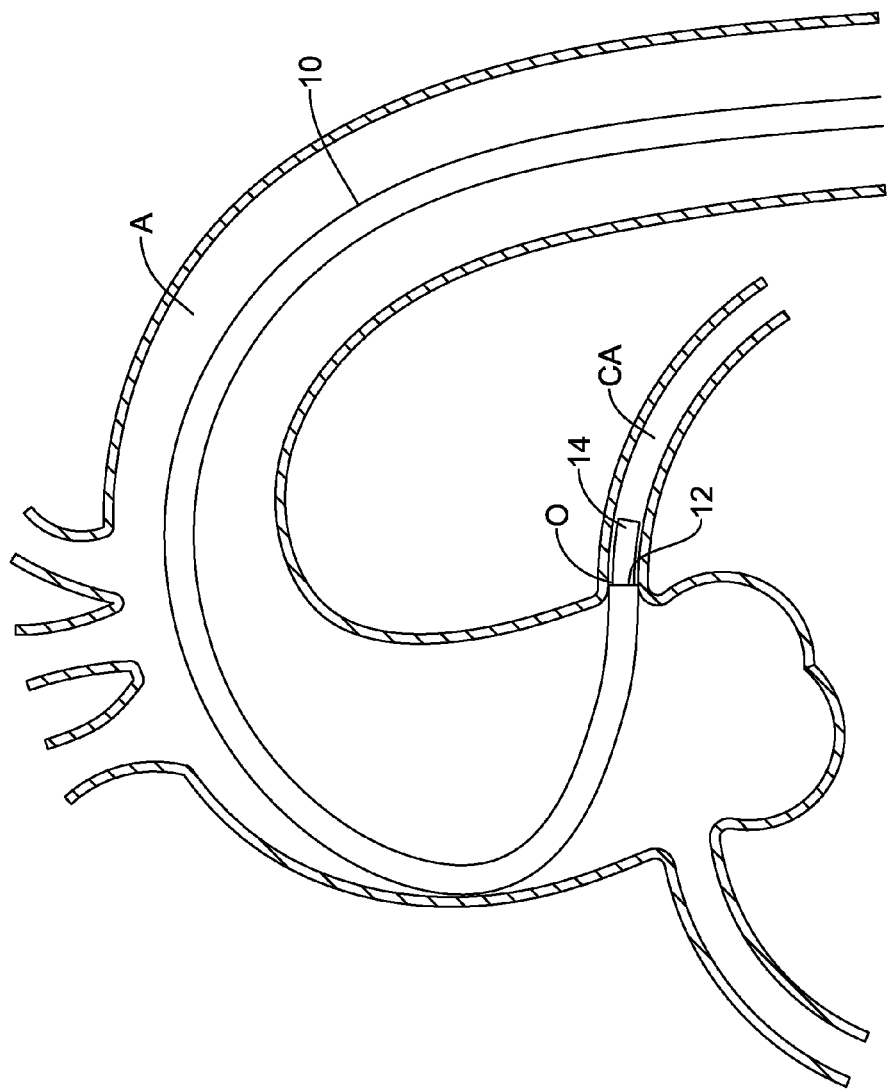
FIG. 2 is a plan view illustrating an example guide extension catheter used in conjunction with a guide catheter.

Disclosed herein are medical devices and methods for making and using medical devices that may improve access to the coronary arteries CA. For example, FIG. 2 illustrates a guide extension catheter 14 extending through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, the extension catheter 14 may stabilize the positioning of guide catheter 10 and allow for improved access to the coronary artery CA for a number of cardiac interventions.

Figure 3:
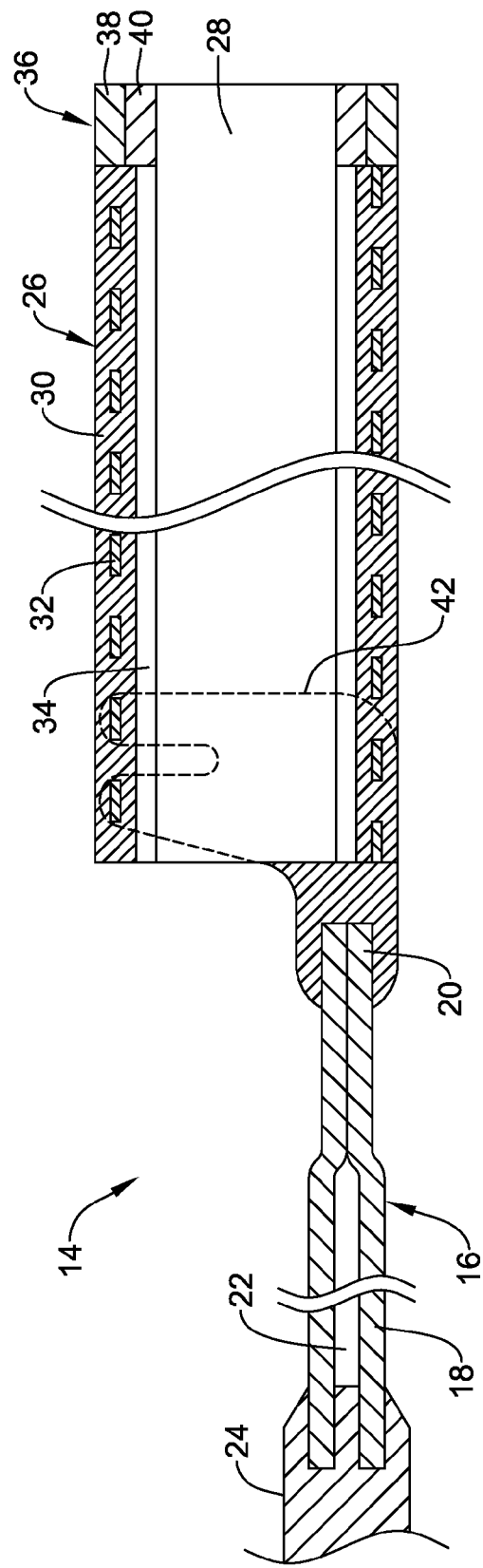
FIG. 3 is a cross-sectional side view of a portion of an example guide extension catheter.

FIG. 3 is a cross-sectional side view of guide extension catheter 14. Here it can be seen that guide extension catheter 14 may include a proximal shaft or member 16. Proximal member 16 may include a proximal portion 18 and a distal or ribbon portion 20. Proximal portion 18 may have a lumen 22 defined therein. In some embodiments, lumen 22 extends along the entire length of proximal portion 18. In other embodiments, lumen 22 extends along only a portion of the length of proximal portion 18. In still other embodiments, ribbon portion 20 may be a solid member or ribbon that lacks a lumen. In addition, proximal portion 18 may include both proximal and distal openings (e.g., positioned at the proximal and distal end of proximal portion 18) such that lumen 22 is "open" on both ends. Alternatively, one or both of the ends of proximal portion 18 may be closed or otherwise sealed. For example, the distal end of proximal portion 18 may be closed. In some of these and in other embodiments, proximal portion 18 may have an opening or port (not shown) formed in the wall of proximal portion 18 and spaced from the proximal and/or distal end of proximal portion 18. The port may or may not be in fluid communication with lumen 22. A hub 24 may be attached to proximal portion 18.

A distal sheath 26 may be attached to proximal member 16. Sheath 26 may have a lumen 28 formed therein. In general, lumen 28 (and/or the inner diameter of distal sheath 26) may be larger than lumen 22 (and/or the inner diameter of proximal portion 18) and may be larger than the outer diameter of proximal member 16. Accordingly, lumen 28 may be sufficiently large so as to allow a therapeutic catheter (e.g., balloon catheter, stent delivery system, etc.) to pass therethrough. For example, when guide extension catheter 14 is positioned within guide catheter 10, the therapeutic catheter may extend within guide catheter 10 alongside proximal member 16 and through lumen 28 of distal sheath 26.

Distal sheath 26 may include a body portion 30. In at least some embodiments, body portion 30 may include one or more polymers including any of those disclosed herein. This may include the use of polymers with a differing durometer along the length of body portion 30. For example, a more proximal section of body portion 30 may include a polymer with a higher durometer and a more distal section of body portion 30 may include a polymer with a lower durometer. Portions of all of the length of body portion may be loaded with or otherwise include a radiopaque material. Body portion 30 may also include a reinforcement member 32.

The form of reinforcement member 32 may vary. For example, reinforcement member 32 may include a braid, coil, mesh, or the like.

An inner liner or layer 34 may be disposed along an inner surface of body portion 30. The form of liner 34 may vary. For example, liner 34 may be a lubricious liner or otherwise include a lubricious material such as polytetrafluoroethylene. A tip member 36 may be attached body portion 30, for example at a distal end of body portion 30. In some embodiments, tip member 36 may be a single layer of material. Alternatively, tip member 36 may include an outer layer 38 and an inner layer 40. In at least some embodiments, tip member 36 may be configured to be generally atraumatic and may include a relatively soft, high compliance material or structure, which may include a polymer or composite material. Outer layer 38 and inner layer 40 may be formed from the same material. In some of these embodiments, outer layer 38 and inner layer 40 may include the same polymeric material and each be loaded with the same or different radiopaque materials. For example, inner layer 40 may include a polyether block amide loaded with approximately 75-95% (e.g., about 90%) by weight tungsten and outer layer 38 may include a polyether block amide loaded with approximately 30-50% (e.g., 40%) by weight bismuth subcarbonate. These are just example. In other embodiments, outer layer 38 and inner layer 40 may be made from different materials.

Distal sheath 26 may be attached to ribbon portion 20 of proximal member 16. The arrangement and/or configuration of the attachment between ribbon portion 20 and distal sheath 26 may vary. For example, distal sheath 26 may have an opening or lumen formed in tube wall thereof and ribbon portion 20 may be disposed within the opening.

This may include necking, skiving, or pinching down ribbon portion 20 and inserting the necked down portion into the opening. In some embodiments, inserting ribbon portion 20 into the opening may secure proximal member 16 to distal sheath 26 via a mechanical bond. In some of these and in other embodiments, additional and/or alternative bonding may be utilized including those bonding mechanisms commonly used for medical devices (e.g., adhesive bonding, welding, thermal bonding, brazing, etc.). Other attachment mechanisms are also contemplated for attaching proximal member 16 to distal sheath 26 including direct bonding (e.g., adhesive bonding, thermal bonding, welding, brazing, etc.), bonding that is facilitated by a third component such as a metal or polymer collar 42 that may be bonded between the ribbon portion 20 and distal sheath 26. For example, collar 42 may be bonded to ribbon portion 20 via welding, thermal bonding, adhesive bonding, or the like. Collar 42 may be bonded to distal sheath 26 using these same methods. For example, collar 42 may be thermally bonded to distal sheath 26 by disposing collar 42 between liner 34 and body portion 30.

Guide extension catheter 14 may also include a number of coatings that may, for example, reduce friction. For example, proximal member 16 and/or distal sheath 26 may have an inner and/or outer coating that includes a hydrophilic polymer that may reduce friction during tracking. An example coating may include BAYER CL-100, BIOSLIDE, NG-HPC, SLIP COAT, MDX, paralyene, or the like. These are just examples. Other materials are contemplated including those disclosed herein.

Figure 4:
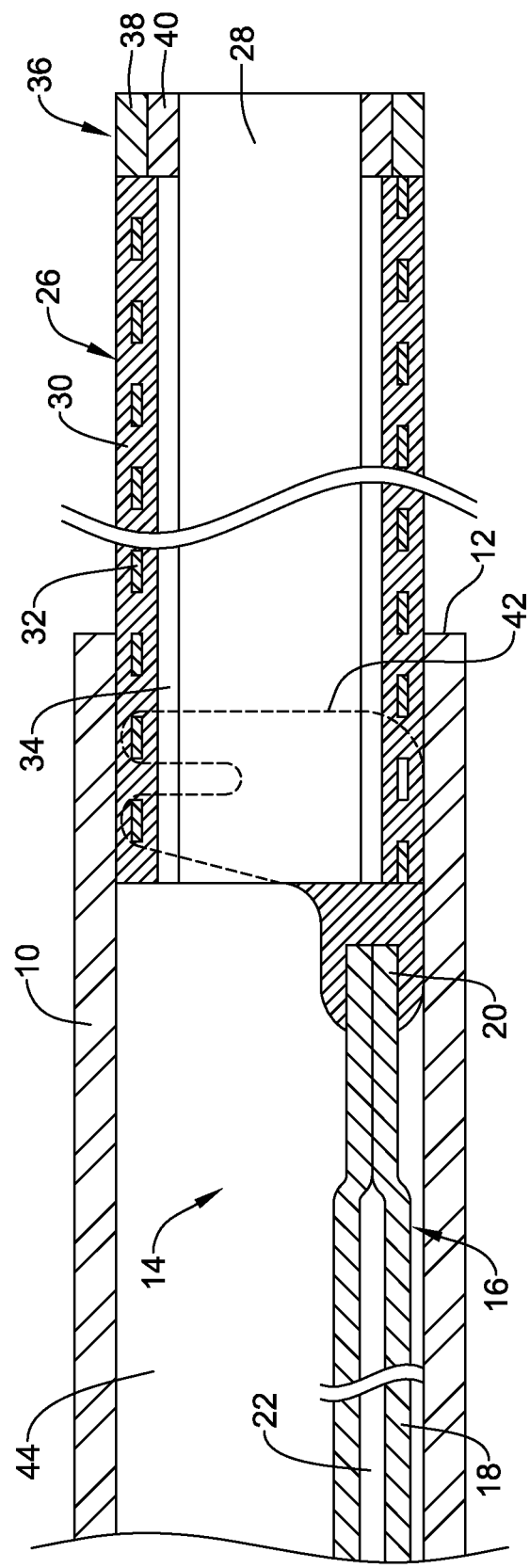
FIG. 4 is a cross-sectional side view of a portion of the example guide extension catheter shown in FIG. 3 and a guide catheter.

FIG. 4 illustrates guide extension catheter 14 disposed within guide catheter 10 (e.g., disposed within a lumen 44 defined within guide catheter 10). As shown, distal sheath 26 may be arranged to extend distally out from distal end 12 of guide catheter 10. When so arranged, distal sheath 26 may engage the ostium O and/or extend within a portion of the coronary artery CA to help maintain the position of guide catheter 10 and improve access to the coronary artery CA. Proximal member 16 may be designed to be sufficiently small (while still being sufficiently sized and configured for pushability) so as to take up relatively little space within the interior or lumen 44 of guide catheter 10. Accordingly, the use of guide extension catheter 14 allows for a therapeutic catheter or medical device to be advanced through guide catheter 10 in order to reach the desired target location for the intervention. In some embodiments, proximal member 16 may contact the inner wall surface of guide catheter 10, which may provide even more space.

Figure 5:
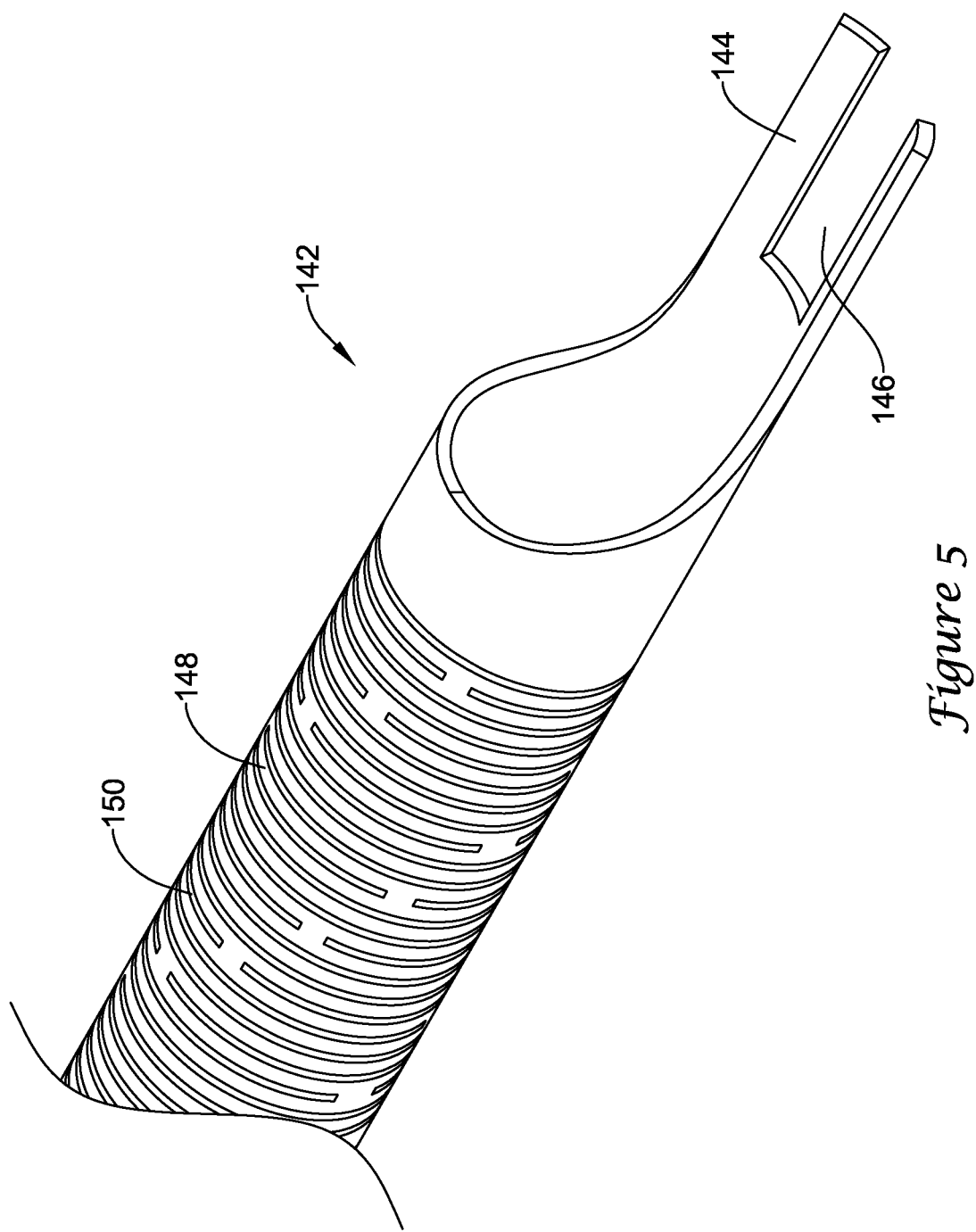
FIG. 5 is a perspective view of an example collar.

While a structure such as collar 42 may be used to attach proximal member 16 to distal sheath 26, other structures are contemplated. For example, FIG. 5 illustrates another example collar 142 that may be similar in form and function to other collars disclosed herein. Collar 142 may be designed to provide a relatively easy connection point between proximal member 16 and distal sheath 26. In addition, because collar 142 may be designed to be structural supportive (e.g., collapse and/or kink resistant) while having a desired level of flexibility, collar 142 may allow guide extension catheters to be manufactured that do not include a reinforcing member (e.g., reinforcing member 32) such as a reinforcing braid, a reinforcing coil, or both. This may desirably impact manufacturing of guide extension catheters.

Figure 6:
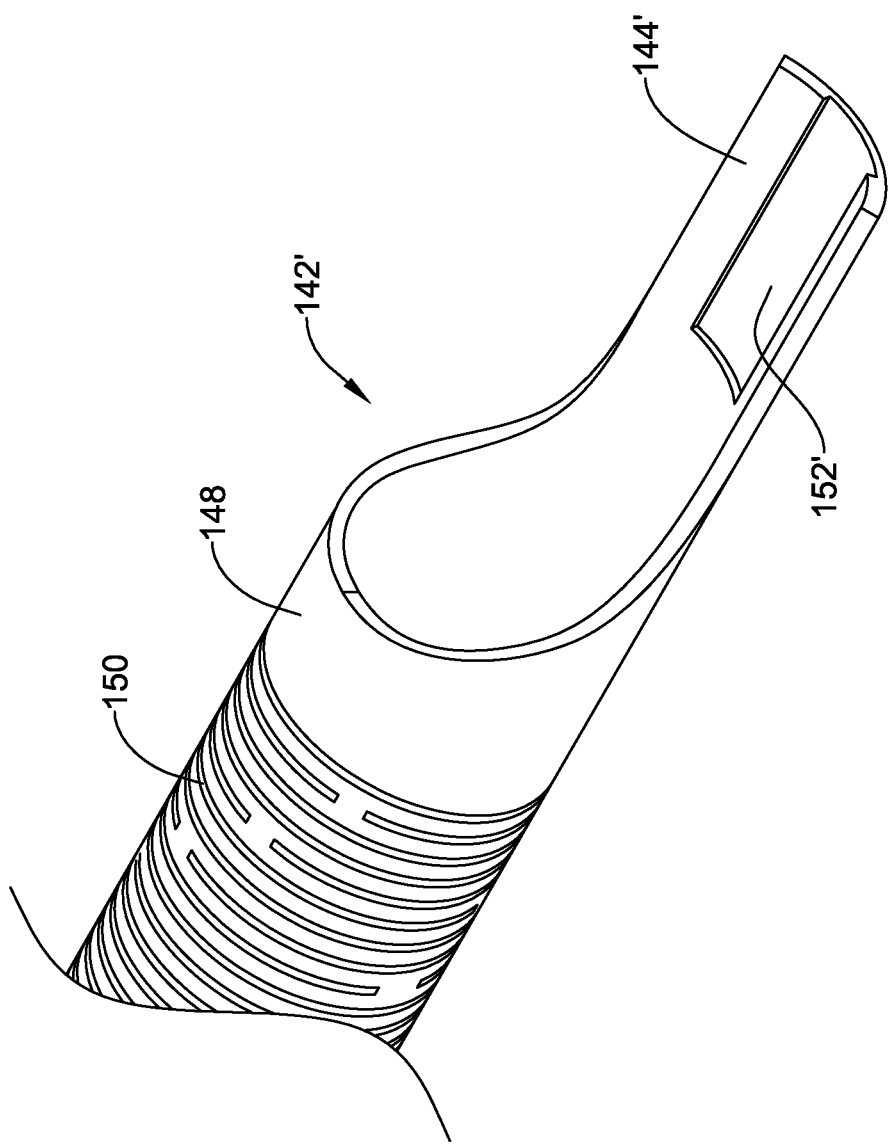
FIG. 6 is a perspective view of another example collar.

Collar 142 may include a proximal or base portion 144. In at least some embodiments, base portion 144 may have a notch or cutout 146 formed therein. Notch 146 may be formed in base portion 144 using a suitable procedure such as laser cutting. Other processes are contemplated. The use of a laser cutting process may be desirable for a number of reasons. For example, laser cutting may allow for a wide variety of structures, shapes, and configurations to be used for notch 146. For example, FIG. 6 illustrates collar 142' having base portion 144' with a ridge or pocket region 152' where a portion of the wall thickness of base portion 144' is removed. Other configurations are contemplated for base portions 144/144'.

Figure 7:
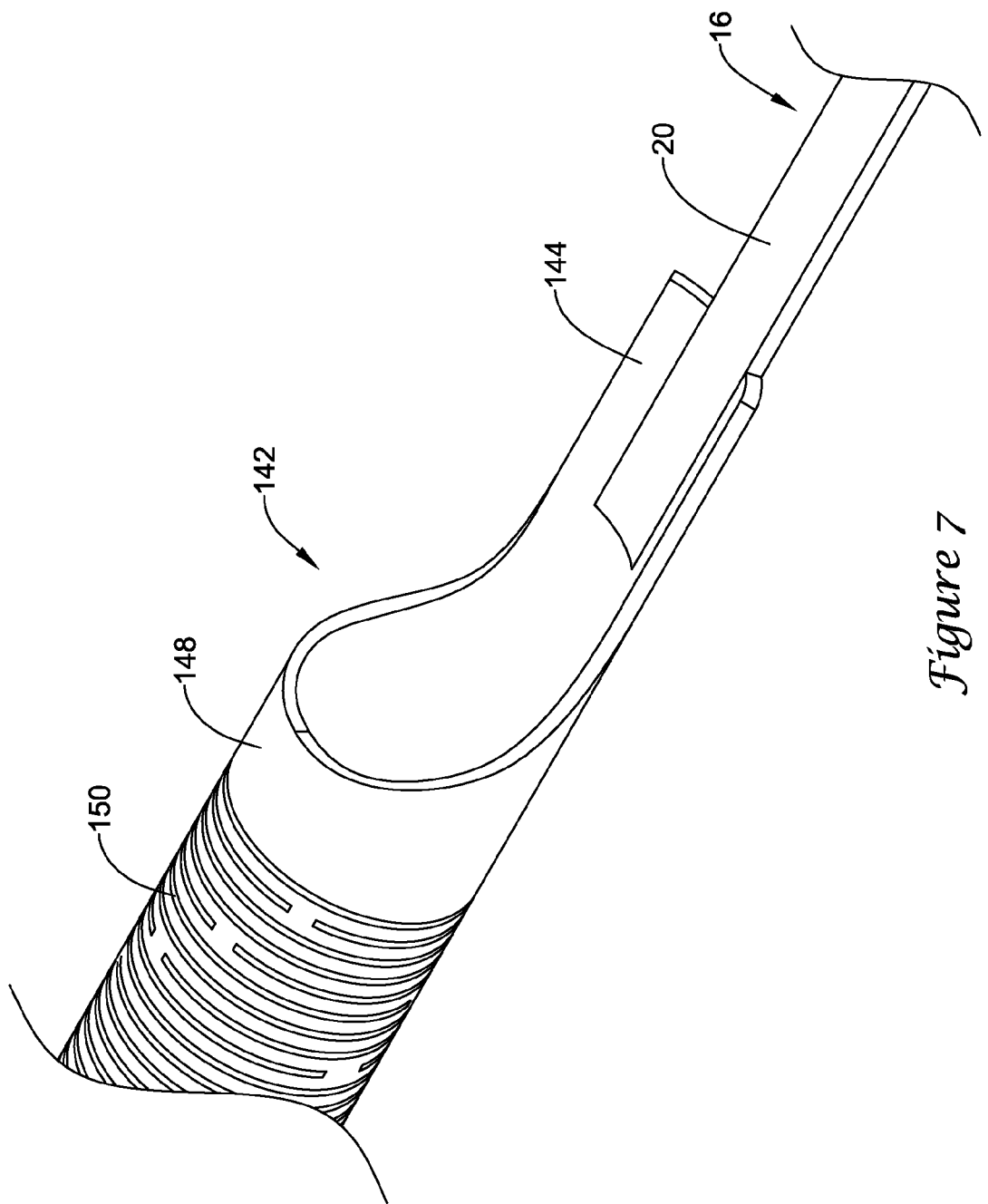
FIG. 7 is a perspective view of an example collar having a ribbon portion coupled thereto.

Base portion 144 (and/or base portion 144') may be secured to ribbon portion 20 of proximal member 16 as shown in FIG. 7. For example, ribbon portion 20 may be inserted into notch 146 and then secured to base portion 144 (and/or base portion 144') using an appropriate bonding technique (e.g., welding, thermal bonding, adhesive bonding, and the like). Securing ribbon portion 20 to base portion 144' may include coining or otherwise machining ribbon portion 20 so that it has a shape corresponding to pocket region 152' so as to allow ribbon portion 20 and base portion 144' to have a corresponding or mating relationship. This may facilitate bonding.

Collar 142 may also include a distal portion 148. In at least some embodiments, distal portion 148 may have a plurality of slots 150 formed therein. The precise form, arrangement, and/or configuration of slots 150 may vary. At least some of the configurations contemplated for slots 150 are disclosed herein. In general, slots 150 may be configured to provide a desirable level of flexibility along distal portion 148. This may include, for example, varying the arrangement and/or configuration of slots 150 along distal portion 148. For example, the number of slots 150 can vary along the length of distal portion 148 so that the flexibility transitions from being less flexible at the proximal end (e.g., fewer slots 150 per unit length) to more flexible at the distal end (e.g., more slots 150 per unit length) of distal portion 148. Other variations in the arrangement and/or configuration of slots 150 may also be utilized to vary the flexibility of distal portion 148 (e.g., variations in slot depth, slot shape, slot arrangement, and the like) along its length (e.g., less flexible adjacent to the proximal end and more flexible adjacent to the distal end). Like notch 146, slots 150 may be formed in distal portion 148 using a laser cutting process. While distal portion 148 is illustrated as having slots 150 formed therein, other configurations are contemplated. For example, distal portion 148 may have a stent-like structure or mesh configuration, may include one or more helical slots or grooves, or the like.

Figure 8:
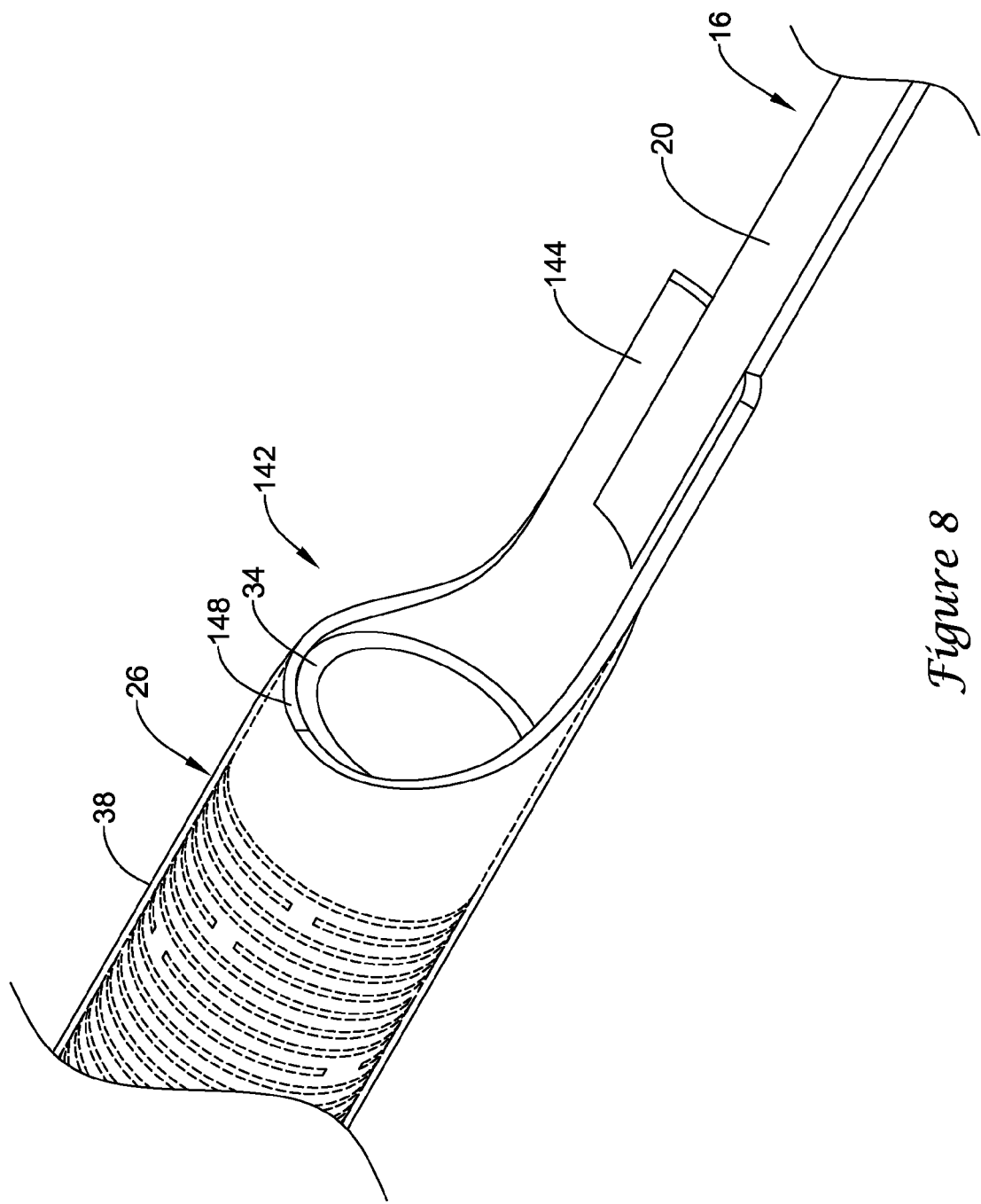
FIG. 8 is a perspective view of an example collar having a ribbon portion coupled thereto and having a distal sheath coupled thereto.

Distal portion 148 may be secured to distal sheath 26 as shown in FIG. 8. This may include disposing distal portion 148 between liner 34 and outer layer 38 and then securing distal portion 148 to distal sheath 26 using an appropriate bonding technique such as thermal bonding.

Figure 9:
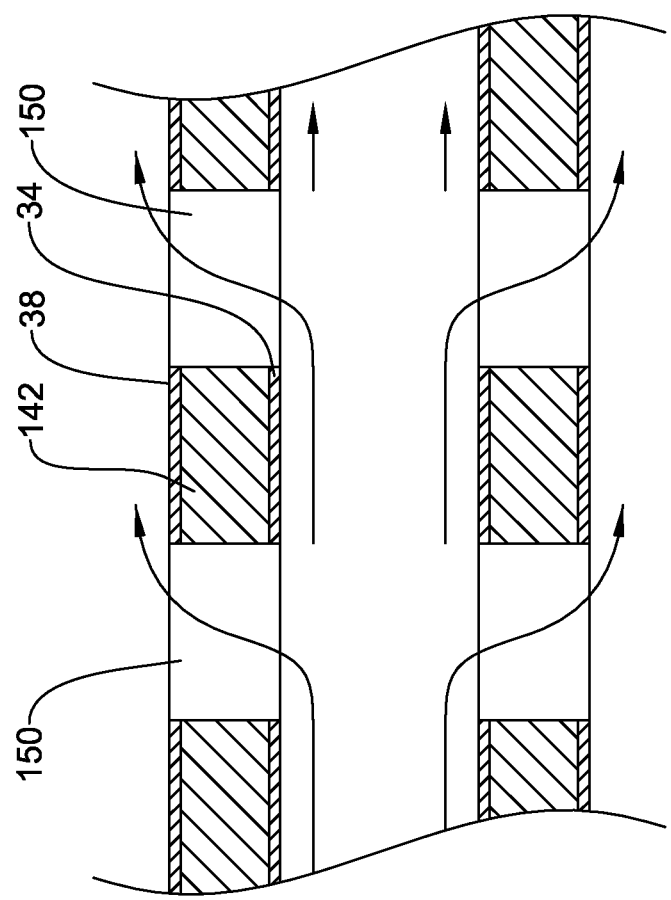
FIG. 9 is a schematic view of fluid flow through an example collar.

In addition to providing desirable flexibility characteristics, slots 150 may be desirable for a number of additional reasons. For example, slots 150 may allow for perfusion therethrough as illustrated in FIG. 9. In order to facilitate perfusion, openings may also be formed in portions of distal sheath (e.g., liner 34 and/or outer layer 38) so that fluid may be permitted to pass between locations along the interior of collar 142 and locations along the exterior of collar 142. This may desirably provide benefits to a number of interventions including interventions within small vessels.

The interior surface, the exterior surface, or both of collar 142 may include one or more coatings including those coatings disclosed herein (e.g., BAYER CL-100, BIO-SLIDE, NG-HPC, SLIP COAT, MDX, paralyene, or the like). Such a coating may be disposed on collar 142 using a suitable process such as chemical vapor deposition or the like. In at least some embodiments, the coating may replace portions or all of liner 34 and/or outer layer 38 of body portion 30. For example, a paralyene coating may be disposed along the interior of collar 142. This coating may be used instead of liner 34. The use of a paralyene liner may be desirable for a number of reasons. For example, a paralyene liner may be thinner than typical inner liners (e.g., PTFE liners), which may desirable impact the profile of the guide extension catheter.

Figure 10:
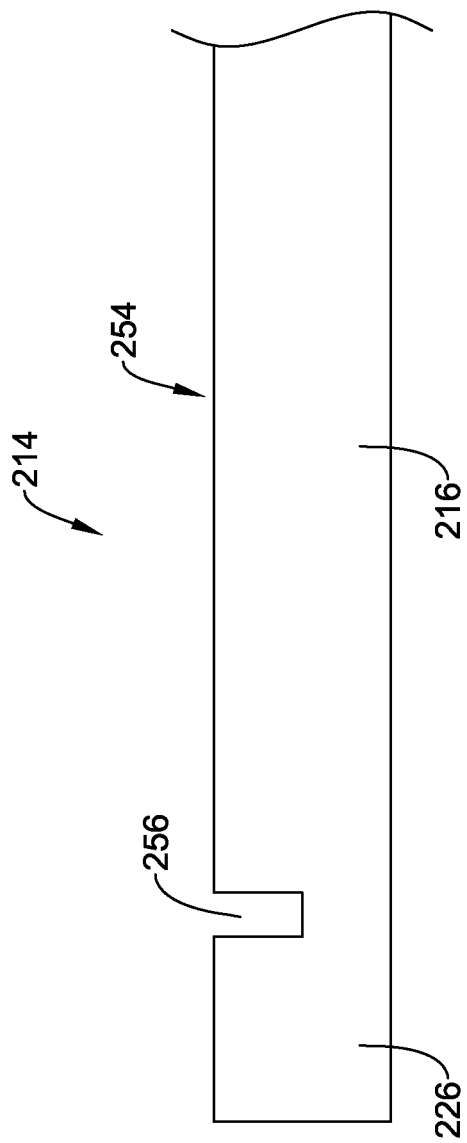
FIG. 10 is a side view of a portion of another example guide extension catheter.

FIG. 10 is a side view of a portion of guide extension catheter 214. Here it can be seen that guide extension catheter 214 may include or otherwise take the form of an elongate tubular member 254. In general, the use of tubular member 254 may be desirable for a number of reasons. For example, tubular member 254 may provide enhanced pushability that allows guide extension catheter 214 to more easily be positioned within guide catheter 10. In addition, tubular member 254 may provide increased resistance to kinking or otherwise provide enhanced control. Collectively, these and other desirable features may allow a user to position guide extension catheter 214 as desired within the vasculature.

Tubular member 254 may have a proximal region 216 and a distal region 226. A slot or slit 256 may be formed in tubular member and may generally be positioned between proximal region 216 and distal region 226. In some embodiments, slot 256 may be positioned approximately half way down the length of tubular member 254 (e.g., so that proximal region 216 and distal region 226 have approximately the same length) or distally therefrom, or slot 256 may be positioned approximately one third of the way down the length of tubular member (e.g., so that proximal region 216 accounts for about two-thirds the length of tubular member 254) or distally therefrom, or slot 256 may be positioned approximately one fourth of the way down the length of tubular member (e.g., so that proximal region 216 accounts for about three-fourths the length of tubular member 254) or distally therefrom, or any other suitable position. In addition, slot 256 may extend through about 10-85% of the diameter of tubular member 254, or about 25-75% of the diameter of tubular member 254, or about 35-65% of the diameter of tubular member 254, or about 50% of the diameter of tubular member 254. These are just examples.

In general, guide extension catheter 214 may be configured so that proximal region 216 can shift between a first configuration and a second or collapsed configuration. This may be desirable for a number of reasons. For example, collapsing proximal region 216 may allow another device (e.g., a treatment device such as a catheter) to be advanced through guide catheter 10 along proximal region 216. Distal region 226 may generally maintain its tubular shape so that it can be positioned within guide catheter 10 so that a portion thereof extends distally from distal end 12 of guide catheter 10 (e.g., as shown in FIG. 2). Accordingly, the treatment device can be advanced through distal region 226 and to a position adjacent an area of interest (e.g., within the coronary artery CA).

Figure 11:
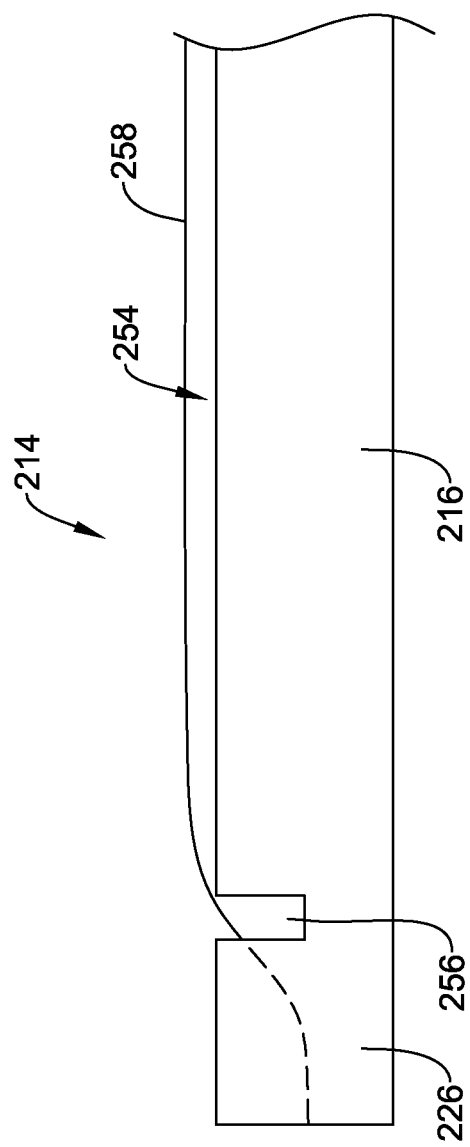
FIG. 11 is a side view of a portion of the example guide extension catheter shown in FIG. 10 and a guidewire.
Figure 12:
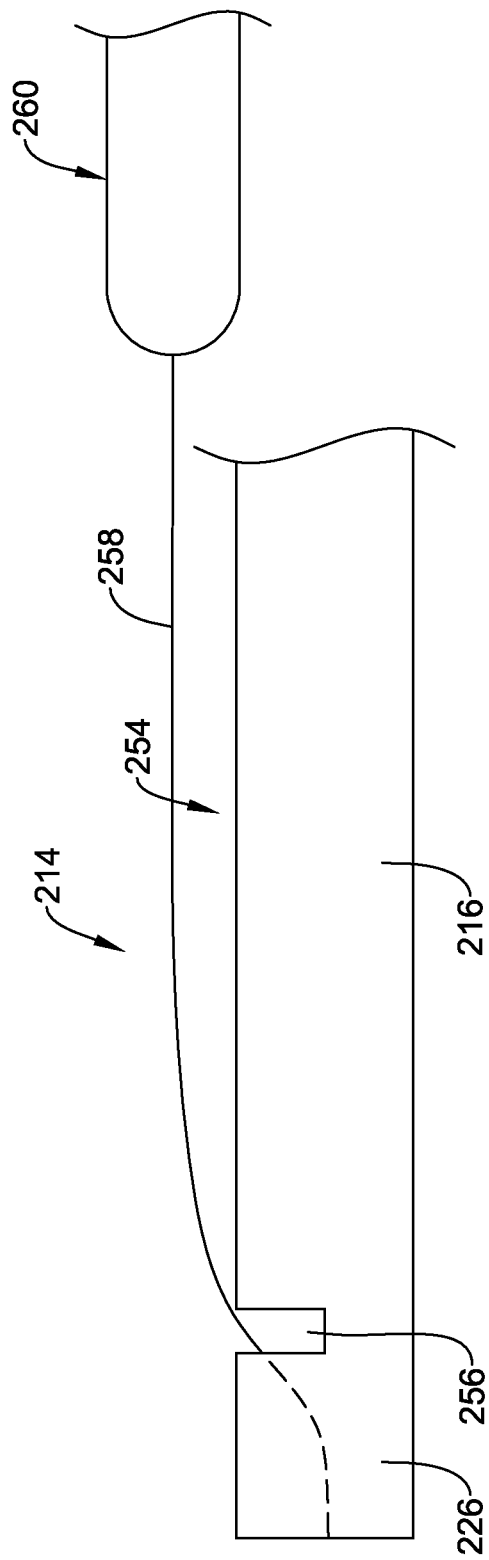
FIG. 12 is a side view of a portion of the example guide extension catheter shown in FIGS. 10-11 and a shaft for shift the guide extension catheter between a first configuration to a collapsed configuration.
Figure 13:
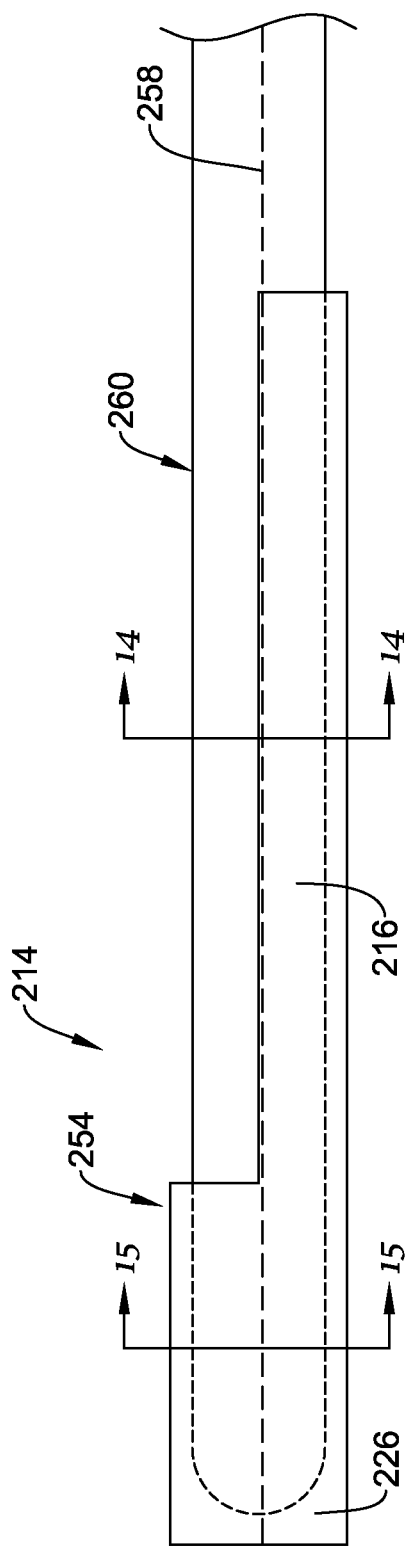
FIG. 13 is a side view of a portion of the example guide extension catheter shown in FIGS. 10-12 with the guide extension catheter shifted to a collapsed configuration.

Shifting proximal region 216 from the first configuration to the collapsed configuration may occur in a variety of different ways. One way of shifting proximal region 216 to the collapsed configuration is illustrated in FIGS. 11-13. For example, FIG. 11 illustrates guide extension catheter 214 along with a guidewire 258. In this example, guidewire 258 extends along an exterior or outer surface of tubular member 254 (e.g., along the outer surface of proximal region 216), through slot 256, and along an inner surface or lumen of distal region 226. Such positioning may be accomplished, for example, by threading distal region 226 over guidewire 258 and pulling guidewire 258 through slot 256.

Figure 15:
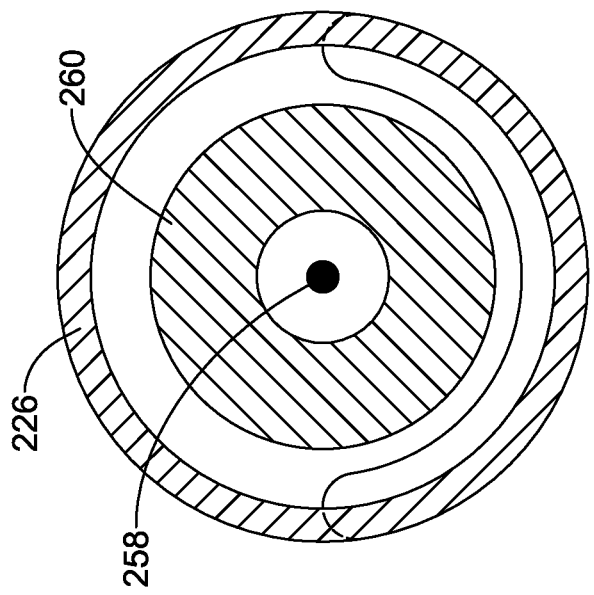
FIG. 15 is a cross-sectional view taken through line 15-15 in FIG. 13.
Figure 14:
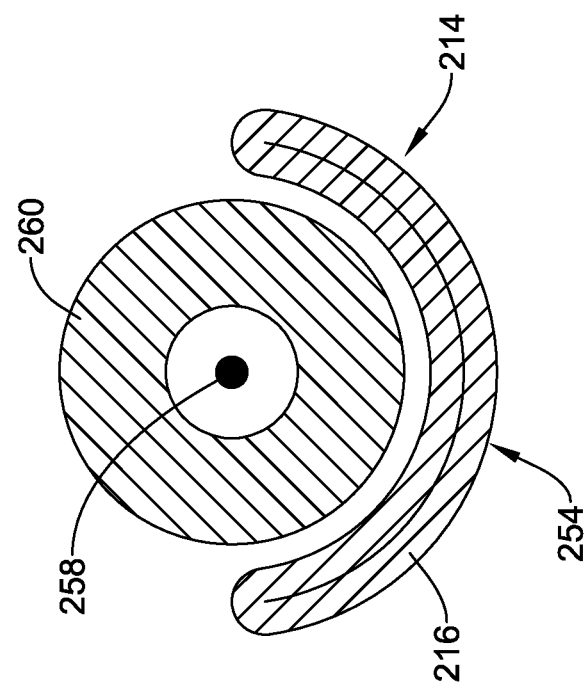
FIG. 14 is a cross-sectional view taken through line 14-14 in FIG. 13.

FIG. 12 illustrates a shaft or generally rigid member 260 being advanced over guidewire 258. In at least some embodiments, shaft 260 may take the form of a catheter, tube, elongated balloon, or mandrel that can be advanced over guidewire 258 and substantially engage or otherwise deflect proximal region 216. For example, as shaft 260 advances over guidewire 258, shaft 260 will engage slot 256. As shaft 260 is further advanced over guidewire 258, shaft 260 may exert a force upon proximal region 216 that will shift proximal region 216 from the first configuration to the collapsed configuration as illustrated in FIG. 13. The force exerted on proximal region 216 may be result of shaft 260 being directed into distal region 226 (which, in at least some embodiment, may include a more rigid material than proximal region 216). Alternatively, the force exerted on proximal region 216 may be "active". For example, shaft 260 may include a balloon (e.g., an elongated balloon) that deflects proximal region 216 when inflated. While in the collapsed configuration, proximal region 216 may be collapsed upon itself and generally have a curved or "U-shape" as shown in FIG. 14. Conversely, shaft 260 will extend through distal region 226 so that distal region 226 will retain its generally tubular shape as shown in FIG. 15.

Figure 16:
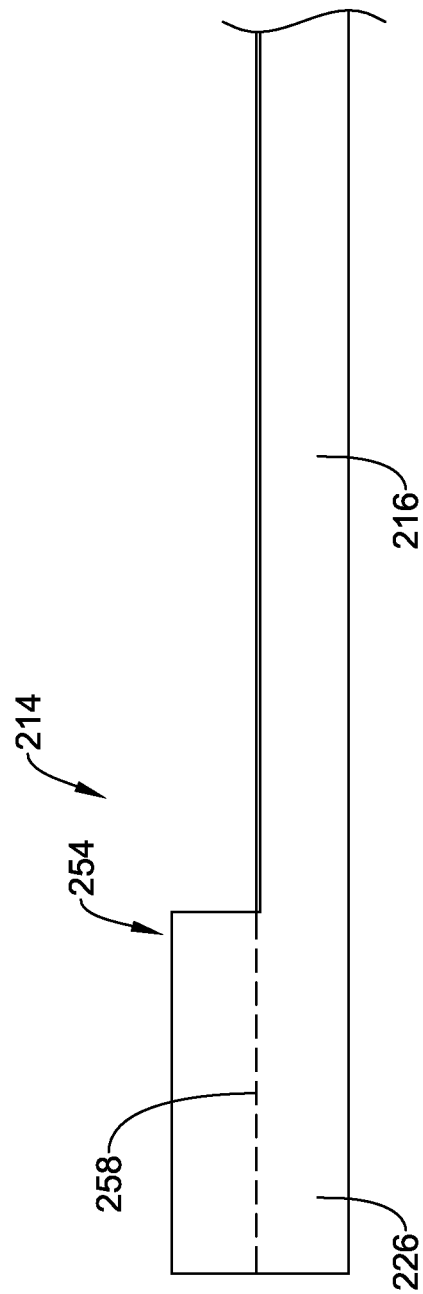
FIG. 16 is a side view of the example guide extension catheter shown in FIGS. 10-15 in a collapsed configuration.
Figure 17:
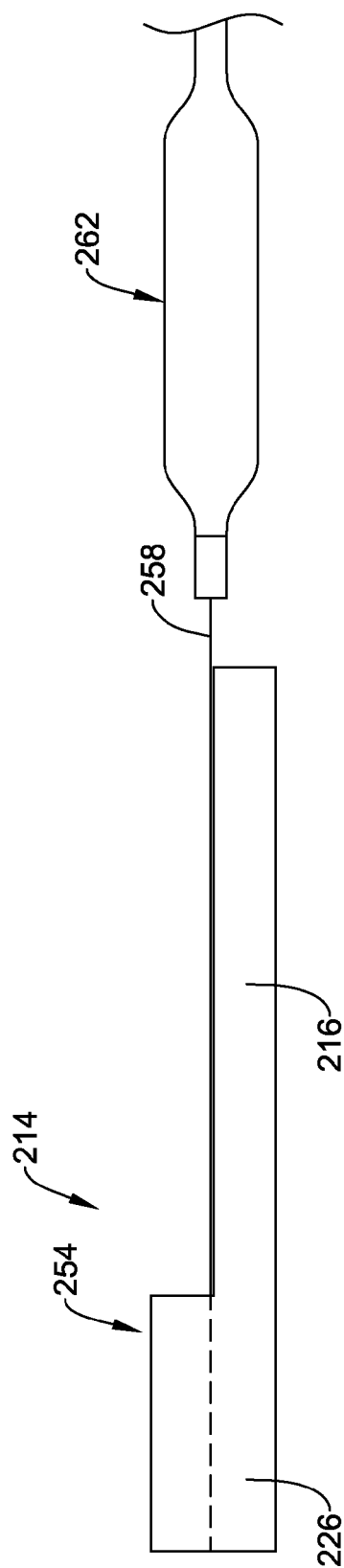
FIG. 17 is a side view of the example guide extension catheter shown in FIGS. 10-16 along with an example treatment device.

In at least some embodiments, proximal region 216 is formed from or otherwise includes a material that plastically deforms when collapsed by shaft 260. Thus, advancing shaft 260 over guidewire 258 may plastically deform or "permanently" collapse proximal region. The resultant configuration may be guide extension catheter 214 having tubular distal region 226 and a collapsed proximal region 216 as shown in FIG. 16. When so configured, a treatment device 262 can be advanced over guidewire 258 as shown in FIG.

17. This may include advancing the treatment device 262 along proximal region 216 and through distal region 226 to a position adjacent to an area of interest. It can be appreciated that the form of the treatment device may vary to include a variety of devices including, but not limited to, catheters, angioplasty balloons and/or catheters, stents or stent delivery systems, ablation catheters, or the like, or other suitable devices.

Figure 18:
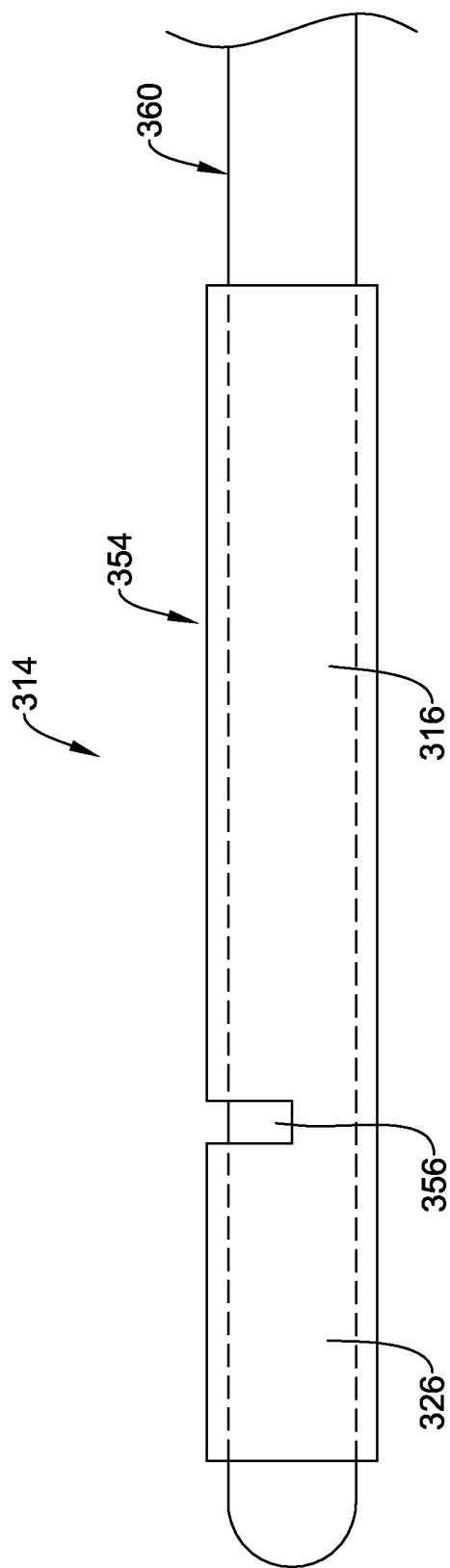
FIG. 18 is a side view of another example guide extension catheter.

FIG. 18 illustrates another example guide extension catheter 314 that may be similar in form and function to other guide extension catheters disclosed herein. Guide extension catheter 314 may include tubular member 354 having proximal region 316, distal region 326, and slot 356. According to this embodiment, proximal region 316 may be configured to be biased into the collapsed configuration. Shaft 360 may be disposed within proximal region 316, distal region 326, or both. When doing so, shaft 360 overcomes the bias and "expands" or otherwise holds proximal region 316 in an expanded configuration. Proximal retraction of shaft 360 may allow proximal region 316 to collapse and take a configuration similar to that of guide extension catheter 214 as shown in FIG. 16. Thereafter, a treatment device may be advanced along proximal region 316 and through distal region 326 to a position adjacent to an area of interest.

Figure 19:
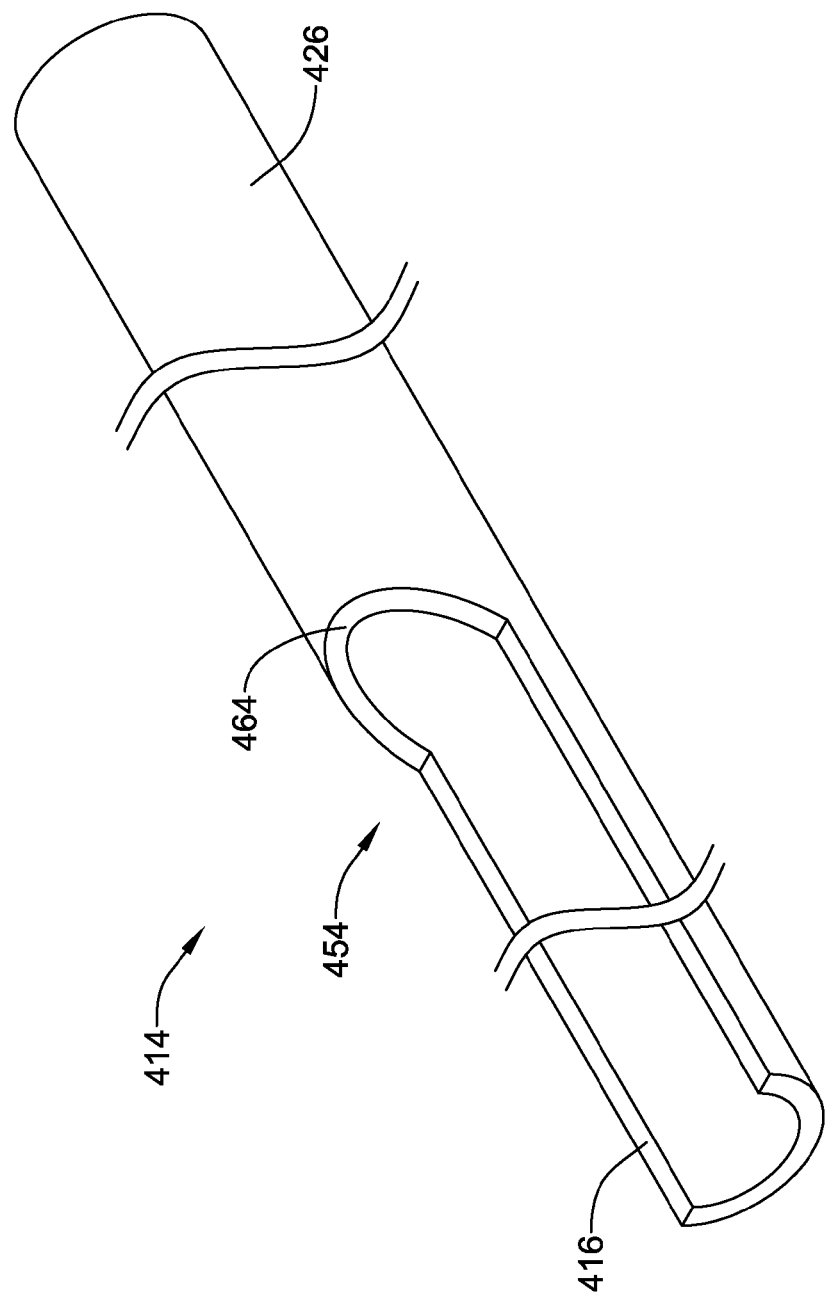
FIG. 19 is a side view of another example guide extension catheter.

FIG. 19 illustrates another example guide extension catheter 414 that may be similar in form and function to other guide extension catheters disclosed herein. Guide extension catheter 414 may include tubular member 454 having proximal portion 416 and distal portion 426. In general, tubular member 454 may be described as a continuous tubular member with a partially circular (and/or partially circumferential) or semicircular proximal portion 416. Proximal portion 416 may also be described as being arcuate, curved, and/or ribbon-like. Tubular member 454 may also include distal portion 426 that may be cylindrical and/or fully circumferential. The continuous wall surface of tubular member 454 may allow for a relatively smooth transition along the length thereof and through a port or opening 464 that may be disposed between proximal portion 416 and distal portion 426. Port 464 may allow a therapeutic medical device to be passed therethrough, into distal portion 426, and to a position adjacent to an area of interest. The continuous nature of tubular member 454 may form a smooth transition in flexibility while reducing the likelihood of kinking. In addition, because the wall surface is continuous, uneven or raised surfaces may be reduced, reducing the likelihood of catching.

While guide extension catheter 414 is show with a partially circumferential proximal portion 416 and a generally cylindrical distal portion 426, other configurations are contemplated. For example, proximal portion 416 may be generally cylindrical and distal portion 426 may be partially circumferential. In addition, one or more additional partially circumferential and/or generally cylindrical portions may be disposed along the length of guide extension catheter 414.

Figure 20:
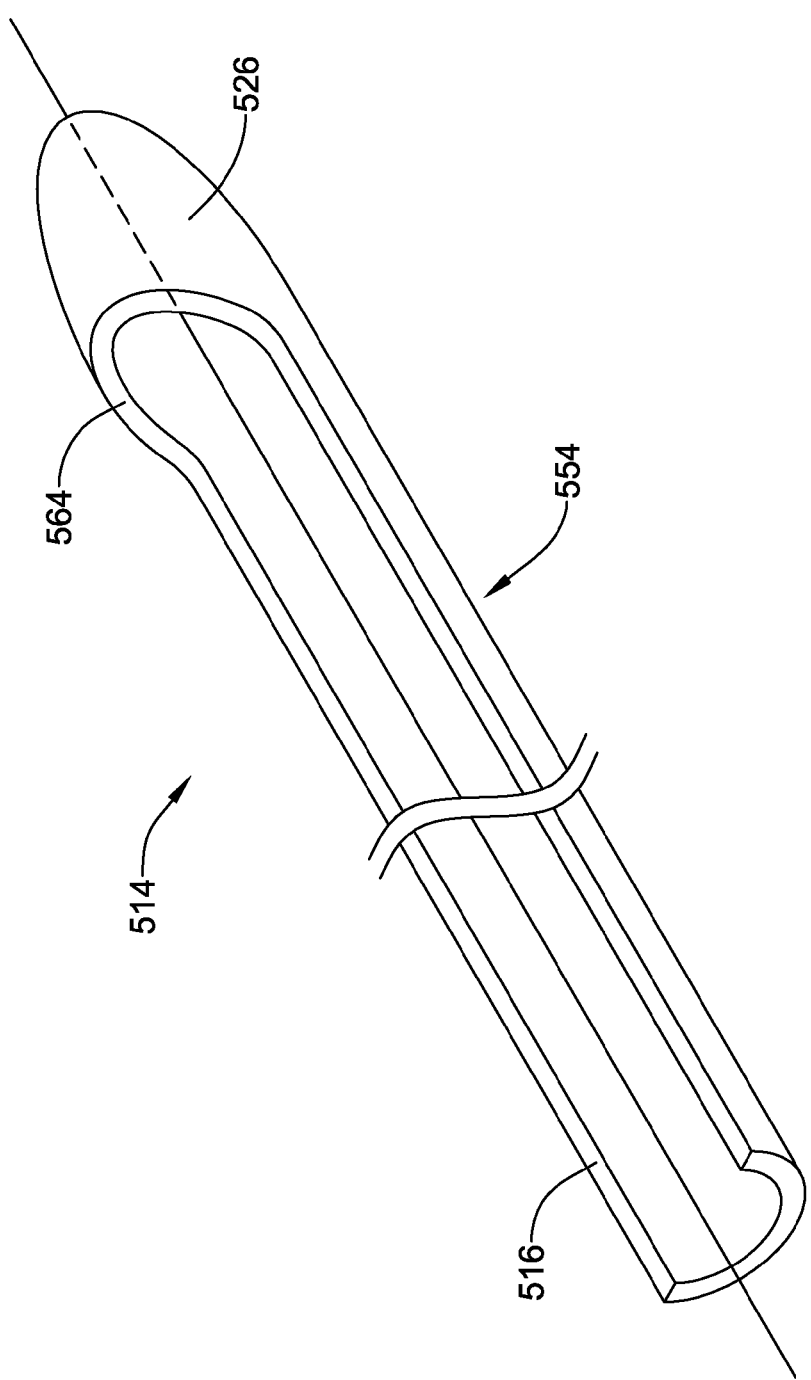
FIG. 20 is a side view of another example guide extension catheter.

FIG. 20 illustrates another example guide extension catheter 514 that may be similar in form and function to other guide extension catheters disclosed herein. Guide extension catheter 514 may include tubular member 554 having proximal portion 516. In at least some embodiments, proximal portion 516 may be only partially circumferential and may extend along substantially the majority of the length of tubular member 554. A tapered tip 526 may be formed at the distal end of proximal portion 516. In at least some embodiments, at least a portion of tapered tip 526 may be fully circumferential. A port or opening 564 may be disposed between proximal portion 516 and tapered tip 526. Tip 526 may be used to track guide extension catheter 514 over a guidewire. In at least some embodiments, tip 526 may have an inner diameter appropriate for passing a therapeutic device therethrough. Alternatively, tip 526 may have an inner diameter that approximates the outer diameter of a typical guidewire. According to these embodiments, guide extension catheter 514 may have a length that is sufficiently long so that the therapeutic device may be passed along proximal portion 516 and out from the distal end 12 of guide catheter 10 (e.g., while a section of proximal portion 516 and/or tip 526 is positioned slightly further distally within the coronary artery CA).

The structure of proximal portion 516 (and/or proximal portion 416) may be desirable for a number of reasons. For example, proximal portion 516 may increase the amount of space within guide catheter 10 (e.g., may reduce the profile of guide extension catheter 414/514). This may allow for larger devices to be passed through guide catheter 10 and/or otherwise improve the deliverability of device passed therethrough by reducing the tracking forces along proximal portion 516 (and/or proximal portion 416).

The materials that can be used for the various components of the guide extension catheters disclosed herein may vary. For simplicity purposes, the following discussion makes reference to proximal member 16 and distal sheath 26. However, this is not intended to limit the devices and methods described herein, as the discussion may be applied to other similar tubular members and/or components of tubular members or devices disclosed herein.

Proximal member 16 and distal sheath 26 and/or other components of guide extension catheter 14 may be made from a metal, metal alloy, polymer (some examples of which are disclosed below), a shape memory polymer, a metal-polymer composite, ceramics, other composites, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-superelastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties. Shape memory polymer materials may also be used for proximal member 16 and/or distal sheath 26 (as well as other components of guide extension catheter 14).

In at least some embodiments, portions or all of proximal member 16 and/or distal sheath 26 may also be loaded with, made of, or otherwise include a radiopaque material. For example, tip member 36 may also include a radiopaque material. Radiopaque materials are understood to be materials capable of producing a relatively bright image on a fluoroscopy screen or another imaging technique during a medical procedure. This relatively bright image aids the user of guide extension catheter 14 in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like. Additionally, other radiopaque marker bands and/or coils may also be incorporated into the design of guide extension catheter 14 to achieve the same result.

In some embodiments, a degree of Magnetic Resonance Imaging (MRI) compatibility is imparted into guide extension catheter 14. For example, proximal member 16 and distal sheath 26, or portions thereof, may be made of a material that does not substantially distort the image and create substantial artifacts (i.e., gaps in the image). Certain ferromagnetic materials, for example, may not be suitable because they may create artifacts in an MRI image. Proximal member 16 and distal sheath 26, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of proximal member 16 and distal sheath 26 that may define a generally smooth outer surface for guide extension catheter 14. In other embodiments, however, such a sheath or covering may be absent from a portion of all of guide extension catheter 14, such that proximal member 16 and distal sheath 26 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guide extension catheter 14 (including, for example, the exterior surface of proximal member 16 and distal sheath 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of proximal member 16 and distal sheath 26, or other portions of guide extension catheter 14. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In addition to variations in materials, various embodiments of arrangements and configurations are also contemplated for slots 150 (and/or other slots disclosed herein) in addition to what is described above. For example, in some embodiments, at least some, if not all of slots 150 are disposed at the same or a similar angle with respect to the longitudinal axis of distal portion 148. As shown, slots 150 can be disposed at an angle that is perpendicular, or substantially perpendicular, and/or can be characterized as being disposed in a plane that is normal to the longitudinal axis of distal portion 148. However, in other embodiments, slots 150 can be disposed at an angle that is not perpendicular, and/or can be characterized as being disposed in a plane that is not normal to the longitudinal axis of distal portion 148. Additionally, a group of one or more slots 150 may be disposed at different angles relative to another group of one or more slots 150. The distribution and/or configuration of slots 150 can also include, to the extent applicable, any of those disclosed in U.S. Pat. Publication No. US 2004/0181174, the entire disclosure of which is herein incorporated by reference. Slots 150 may be provided to enhance the flexibility of distal portion 148 while still allowing for suitable torque transmission characteristics. Slots 150 may be formed such that one or more rings and/or tube segments interconnected by one or more segments and/or beams that are formed in distal portion 148, and such tube segments and beams may include portions of distal portion 148 that remain after slots 150 are formed in distal portion 148. Such an interconnected structure may act to maintain a relatively high degree of torsional stiffness, while maintaining a desired level of lateral flexibility. In some embodiments, some adjacent slots 150 can be formed such that they include portions that overlap with each other about the circumference of distal portion 148. In other embodiments, some adjacent slots 150 can be disposed such that they do not necessarily overlap with each other, but are disposed in a pattern that provides the desired degree of lateral flexibility.

Additionally, slots 150 can be arranged along the length of, or about the circumference of, distal portion 148 to achieve desired properties. For example, adjacent slots 150, or groups of slots 150, can be arranged in a symmetrical pattern, such as being disposed essentially equally on opposite sides about the circumference of distal portion 148, or can be rotated by an angle relative to each other about the axis of distal portion 148. Additionally, adjacent slots 150, or groups of slots 150, may be equally spaced along the length of distal portion 148, or can be arranged in an increasing or decreasing density pattern, or can be arranged in a non-symmetric or irregular pattern. Other characteristics, such as slot size, slot shape, and/or slot angle with respect to the longitudinal axis of distal portion 148, can also be varied along the length of distal portion 148 in order to vary the flexibility or other properties. In other embodiments, moreover, it is contemplated that the portions of the tubular member, such as a proximal section, or a distal section, or the entire distal portion 148, may not include any such slots 150.

As suggested herein, slots 150 may be formed in groups of two, three, four, five, or more slots 150, which may be located at substantially the same location along the axis of distal portion 148. Alternatively, a single slot 150 may be disposed at some or all of these locations. Within the groups of slots 150, there may be included slots 150 that are equal in size (i.e., span the same circumferential distance around distal portion 148). In some of these as well as other embodiments, at least some slots 150 in a group are unequal in size (i.e., span a different circumferential distance around distal portion 148). Longitudinally adjacent groups of slots 150 may have the same or different configurations. For example, some embodiments of distal portion 148 include slots 150 that are equal in size in a first group and then unequally sized in an adjacent group. It can be appreciated that in groups that have two slots 150 that are equal in size and are symmetrically disposed around the tube circumference, the centroid of the pair of beams (i.e., the portion of distal portion 148 remaining after slots 150 are formed therein) is coincident with the central axis of distal portion 148. Conversely, in groups that have two slots 150 that are unequal in size and whose centroids are directly opposed on the tube circumference, the centroid of the pair of beams can be offset from the central axis of distal portion 148. Some embodiments of distal portion 148 include only slot groups with centroids that are coincident with the central axis of the distal portion 148, only slot groups with centroids that are offset from the central axis of distal portion 148, or slot groups with centroids that are coincident with the central axis of distal portion 148 in a first group and offset from the central axis of distal portion 148 in another group. The amount of offset may vary depending on the depth (or length) of slots 150 and can include other suitable distances.

Slots 150 can be formed by methods such as micromachining, saw-cutting (e.g., using a diamond grit embedded semiconductor dicing blade), electrical discharge machining, grinding, milling, casting, molding, chemically etching or treating, or other known methods, and the like. In some such embodiments, the structure of the distal portion 148 is formed by cutting and/or removing portions of the tube to form slots 150. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing catheter 14 may include forming slots 150 in distal portion 148 using these or other manufacturing steps.

In at least some embodiments, slots 150 may be formed in tubular member using a laser cutting process. The laser cutting process may include a suitable laser and/or laser cutting apparatus. For example, the laser cutting process may utilize a fiber laser. It should be understood that this disclosure is, in many respects, only illustrative.

Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A guide extension catheter, comprising:
   an elongate tubular member having a proximal region, a distal region, and a lumen extending therethrough, the proximal region configured to shift in a radial direction between a first configuration and a collapsed configuration;
   a slot formed in the tubular member and extending to the lumen between the proximal region and the distal region, the slot configured to accommodate a guidewire therethrough when the proximal region of the tubular member is in the first configuration; and
   an elongate shaft for shifting the proximal region between the first configuration and the collapsed configuration, the elongate shaft shifting the proximal region from the first configuration to the collapsed configuration by being advanced along a guidewire extending through the slot.

2. The guide extension catheter of claim 1, wherein the proximal region has a U-shape when in the collapsed configuration.

3. The guide extension catheter of claim 1, further comprising a guidewire extending along an exterior of the proximal region, through the slot, and within the distal region of the tubular member.

4. The guide extension catheter of claim 3, wherein advancing the shaft over the guidewire shifts the proximal region from the first configuration to the collapsed configuration.

5. The guide extension catheter of claim 4, wherein the shaft plastically deforms the proximal region such that the proximal region remains in the collapsed configuration even after the shaft is withdrawn from the proximal region.

6. A method for using a guide extension catheter, the method comprising:
   providing a guide catheter;
   advancing the guide catheter through a body lumen to a position adjacent to an area of interest;
   advancing a guide extension catheter through the guide catheter, the guide extension catheter comprising:
      an elongate tubular member having a proximal region, a distal region, and a slot formed in the tubular member between the proximal region and the distal region, wherein the proximal region of the tubular member is configured to shift between a first configuration and a collapsed configuration, and
      an elongate shaft for shifting the proximal region between the first configuration and the collapsed configuration;
   shifting the proximal region from the first configuration to the collapsed configuration;
   advancing a treatment device along an exterior surface of the proximal region of the tubular member in the collapsed configuration and through the distal region of the tubular member to the position adjacent to the area of interest; and
   disposing a guidewire along an exterior surface of the proximal region, through the slot, and within the distal region,
   wherein shifting the proximal region from the first configuration to the collapsed configuration includes advancing the shaft over the guidewire.

7. The method of claim 6, wherein the proximal region has a U-shape when in the collapsed configuration.

8. The method of claim 6, wherein the shaft plastically deforms the proximal region such that the proximal region remains in the collapsed configuration.

9. The method of claim 6, wherein advancing the guide extension catheter through the guide catheter includes disposing a portion of the distal region of the guide extension catheter distally beyond a distal end of the guide catheter.

10. The method of claim 9, wherein the portion of the distal region of the guide extension catheter extending distally beyond the distal end of the guide catheter extends through an ostium of a coronary artery.

11. A guide extension catheter system, the system comprising:
   a guide catheter;
   a guide extension catheter configured to extend through the guide catheter, the guide extension catheter comprising:
      an elongate tubular member having a lumen, a proximal region configured to shift between a first configuration and a collapsed configuration, a distal region, and a slot formed in the tubular member and extending to the lumen between the proximal region and the distal region, the slot configured to accommodate a guidewire therethrough when the proximal region is in the first configuration, and
      an elongate shaft for shifting the proximal region between the first configuration and the collapsed configuration;
   a treatment catheter configured to extend through the guide catheter and through the distal region of the elongate tubular member after the elongate shaft has been used to shift the proximal region into the collapsed configuration;
   a guidewire extending along an exterior of the proximal region, through the slot, and within the distal region of the tubular member;

wherein advancing the shaft over the guidewire shifts the proximal region from the first configuration to the collapsed configuration; and wherein the shaft plastically deforms the proximal region such that the proximal region remains in the collapsed configuration.

\* \* \* \* \*